US008735373B2

(12) United States Patent
Pizzoni

(10) Patent No.: US 8,735,373 B2
(45) Date of Patent: May 27, 2014

(54) GLYCOSAMINOGLYCAN ORAL USE AND COMPOSITIONS

(75) Inventor: Angelo Pizzoni, Arona (IT)

(73) Assignee: Apharm S.R.L., Arona (IT)

( * ) Notice: Subject to any disclaimer, the term of this patent is extended or adjusted under 35 U.S.C. 154(b) by 537 days.

(21) Appl. No.: 12/991,776

(22) PCT Filed: May 8, 2009

(86) PCT No.: PCT/IB2009/005549
§ 371 (c)(1), (2), (4) Date: Nov. 24, 2010

(87) PCT Pub. No.: WO2009/138843
PCT Pub. Date: Nov. 19, 2009

(65) Prior Publication Data

US 2011/0071106 A1 Mar. 24, 2011

(30) Foreign Application Priority Data

May 13, 2008 (WO) .................. PCT/IB2008/001181

(51) Int. Cl.
*A01N 43/04* (2006.01)
*A61K 31/715* (2006.01)

(52) U.S. Cl.
USPC ........................................................... 514/54

(58) Field of Classification Search
None
See application file for complete search history.

(56) References Cited

U.S. PATENT DOCUMENTS

| | | | | |
|---|---|---|---|---|
| 2003/0212005 | A1 * | 11/2003 | Petito et al. | 514/21 |
| 2003/0232100 | A1 | 12/2003 | Theoharides | |
| 2005/0182022 | A1 | 8/2005 | Pierce | |
| 2008/0003257 | A1 | 1/2008 | Marcum et al. | |

FOREIGN PATENT DOCUMENTS

| | | |
|---|---|---|
| EP | 1 243 260 | 9/2002 |
| EP | 1 308 164 | 5/2003 |
| WO | WO 02/09728 | 2/2002 |
| WO | WO 03/090763 | 11/2003 |

OTHER PUBLICATIONS

International Search Report for PCT/IB2009/005549, mailed Jan. 13, 2010.
Written Opinion of the International Searching Authority for PCT/IB2009/005549, mailed Jan. 13, 2010.
International Preliminary Report on Patentability with Two Amended Sheets for PCT/IB2009/005549, dated Aug. 4, 2010.

* cited by examiner

*Primary Examiner* — Layla Bland
(74) *Attorney, Agent, or Firm* — Nixon & Vanderhye PC

(57) ABSTRACT

The present invention concerns the use of a glycosaminoglycan association of hyaluronic acid and chondroitin sulfate for the preparation of oral compositions for the prevention or for the treatment of upper gastro-intestinal tract disorders and for the preparation of upper gastro-intestinal epithelial damage, as well as the oral compositions comprising said glycosaminoglycan association.

11 Claims, No Drawings

GLYCOSAMINOGLYCAN ORAL USE AND COMPOSITIONS

This application is the U.S. national phase of International Application No. PCT/IB2009/005549 filed 8 May 2009, which designated the U.S. and claims priority to IB Application No. PCT/IB2008/001181 filed 13 May 2008, the entire contents of each of which are hereby incorporated by reference.

FIELD OF THE INVENTION

The present invention concerns the use of a glycosaminoglycan association of hyaluronic acid and chondroitin sulfate for the preparation of oral compositions for the prevention or for the treatment of upper gastro-intestinal tract disorders and for the reparation of upper gastro-intestinal epithelial damage. More particularly, the oral compositions thus prepared are for the prevention or for the treatment of gastritis and of esophagitis caused in particular by gastric reflux or for the treatment of esophagus endothelial damages.

The invention also concerns practically protein-free oral compositions for the prevention or for the treatment of upper gastro-intestinal tract disorders comprising a glycosaminoglycan association of hyaluronic acid and chondroitin sulfate in admixture with a pharmaceutical carrier, in oral, preferably liquid, compositions also comprising at least one bioadhesive agent.

BACKGROUND OF THE INVENTION

Glycosaminoglycans are a family of polysaccharides formed by the repetition of a uronic acid, glucuronic or iduronic acid, $\alpha$ 1→4 or $\beta$ 1→3 linked to a hexosamine residue, glucosamine or galactosamine. Hexosamine and uronic acid residues can be variously sulfated. Beside heparin and heparan sulfate, also dermatan sulfate, hyaluronic acid and chondroitin sulfate are included into glycosaminoglycans' family. Physiologically, glycosaminoglycans are organized in proteoglycans, formed by a protein core wherein the glycosaminoglycan is linked by a linkage region. These structures are in charge of the control of biochemical reactions by the uptake and the release of proteins and growth factors (J. F. Kennedy, C. A. White, Bioactive Carbohydrates, 1983, Ellis Horwood Ltd, 211-227).

In particular, chondroitin sulfate is located in cartilages and the epithelia like gastric mucosa or urethelium. In the cartilages it gives elasticity and controls the resistance, while in mucosa and epithelia protects the epithelium itself from the acid aggression in the case of gastric epithelium or by potassium in the case of urethelium. In the pathologies in which the amount of chondroitin sulfate is low such as gastritis or interstitial cystitis the administration of chondroitin sulfate helps to mitigate the inflammation and the correlate damages due to the low chondroitin sulfate content. Extractive chondroitin sulfate normally has an average molecular weight from 10,000 to 50,000 Da. Biosynthetic chondroitin sulfate may be obtained starting from K4 polysaccharide, for example according to the method described in EP 1304338. Its average molecular weight is from 12,000 to 15,000 Da, even though lower or higher molecular weight products may be prepared.

Hyaluronic acid naturally occurs as a regular unsulfated macromolecule formed by a linear disaccharidic sequence of glucuronic acid 1-3 linked to N-acetylglucosamine, while chondroitin sulfate is mainly present in two distinct forms chondroitin-4-sulfate (or ChSA) and chondroitin-6-sulfate (or ChSC). Chondroitin sulfate is formed by disaccharide repetition containing glucuronic acid $\beta$1→3 linked to galactosamine that is sulfated or in position 4 or in position 6. Clusters of ChSA and ChSC are present in the same molecule. Occasionally low amount of disulfated and non sulfated disaccharides can be also present within the polysaccharide chain. The proteoglycans containing chondroitin sulfate are formed by a hyaluronic acid backbone onto which protein chains (protein core) bearing branches of condroitin sulfate chains are grafted. A highly viscous macromolecule is thus formed whose viscosity is due to the very high molecular mass and also to the structural characteristics of its components.

Extractive hyaluronic acid has an average molecular weight of the order of $10^5$-$10^6$ Da.

Unless otherwise specified, in the present description the term "hyaluronic acid" and "chondroitin sulfate" designates hyaluronic acid and chondroitin sulfate in sodium salt form, the dosages given herein below being referred to sodium hyaluronate and sodium chondroitin sulfate.

PRIOR ART

EP 136782 discloses an association of hyaluronic acid, or the sodium, potassium, magnesium and calcium salt thereof, and chondroitin sulfate, or the sodium, potassium, magnesium or calcium salt thereof, used for the treatment of interstitial cystitis This document generally mentions associations in an aqueous buffer at pH of 7 to 8 wherein the concentration of the active components is of from 0.1 to 10% but specifically discloses compositions in which 5.3 percent by weight of the total composition is chondroitin sulfate and 4.2 percent is hyaluronate.

U.S. 2006/234978 describes the use of a solution containing both hyaluronic acid and chondroitin sulfate (optionally also with glucosamine) to treat the interstitial cystitis. The amounts of chondroitin sulfate and of hyaluronic acid disclosed therein are 0.5-1.5 g and 10-50 mg, respectively, per dosage unit.

U.S. 2004/0224384 (see also U.S. 2003/0091652, U.S. Pat. No. 6,780,841 and U.S. Pat. No. 7,091,180) discloses an enzymatically hydrolyzed collagen type II, orally or topically used for treating connective tissue disorders and replenishing skin viscoelasticity. Said hydrolyzed collagen is obtained from chicken sternal cartilage, and consists of a mixture of fragments having an average molecular weight of between about 50 to about 10,000 Da containing 67% protein (12.1% total nitrogen), 18% carbohydrate and 0.1% fat. The carbohydrate portion is mainly formed by depolymerized chondroititin sulfate and hyaluronic acid, (at least 20% and at least 10%, respectively, of the whole hydrolyzed collagen) and by proteoglycans (3% of the whole hydrolyzed collagen).

U.S. 2005182022 (see also U.S. Pat. No. 6,924,273) discloses chondroprotective/restorative compositions, to be administered especially as animal feed to racing thoroughbreds, comprising hyaluronic acid, alone or in association with chondroitin sulfate and/or glucosamine, together with a gelling agent such as a cellulose derivative. In particular, the document describes a composition comprising 1% wt. of sodium hyaluronate, 4% wt. of condroitin sulfate and 1% sodium carboxymethyl cellulose and unit forms comprising 200 mg of chondroitin sulfate and 100 mg of hyaluronic acid. In human, the daily recommended dose is of from 7 to 40 mg of hyaluronic acid.

WO 00/67799 (see also EP 1173218, EP 1614431 and U.S. Pat. No. 6,610,667) discloses a composition for the prevention or treatment of esophagus disorders caused by reflux, comprising an alginate and two types of gums (xantan/carrageenan and galactomannan/glucomannan gums). This composition has high bioadhesive properties and is capable of detachably adhering to desired regions of the esophagus, thus providing a protective and a direct healing effect. However, the disclosed compositions are very viscous because, even in the case of liquid preparations, the viscosity ranges from 500 to 10,000 mPa.

It is also well known that chondroitin sulfate is an effective inhibitor of pepsin induced damage of the gastroduodenal mucosa having gastroduodenal ulcer healing properties (see for example Crandall L. A et al., Proc. Soc Exp. Biol. Medd 30, 704-708, 1933).

SUMMARY OF THE INVENTION

It has been found that an association of chondroitin sulfate and hyaluronic acid may be used for the preparation of medicaments for combating upper gastro-intestinal tract disorders. These disorders, in particular gastritis, gastroduodenitis and esophagitis are generally due to hyperacidity or to adverse effects of drugs. The medicaments are oral compositions for the prevention or treatment of upper gastro-intestinal tract disorders and for the reparation of related, damaged epithelial tissues. In particular, it has been found that oral compositions prepared by using an association of chondroitin sulfate and hyaluronic acid, in admixture with a pharmaceutical carrier, prevent esophagitis in case of gastric reflux or allow the treatment of esophagitis or of pathologies in which the esophagus epithelial damage is due to adverse effects of drugs.

It has also been found that by associating chondroitin sulfate and hyaluronic acid in a pharmaceutical carrier comprising at least one water soluble bioadhesive agent, novel oral liquid compositions with a viscosity from 30 to 100 mPa suitable for an easy administration to humans are obtained which are extremely efficacious in preventing or treating esophagitis.

The expression "practically protein-free", referred to the compositions of the present invention indicates that the active ingredients contained therein are purified products, containing less than 1% protein.

DETAILED DESCRIPTION

It is an object of the present invention to provide the use of an association of chondroitin sulfate or of a pharmaceutically acceptable salt thereof and hyaluronic acid or of a pharmaceutically acceptable salt thereof for the preparation of medicaments for combating upper gastro-intestinal disorders in human, in particular for the preparation of oral (edible) compositions for the prevention or the treatment of upper gastrointestinal disorders. In particular, said medicaments are oral compositions It is also an object of the present invention to provide a method for preventing or treating upper gastro-intestinal tract disorders in humans, which comprises administering to said human in need of said prevention or treatment, an effective amount of an oral composition comprising chondroitin sulfate and hyaluronic acid in admixture with a pharmaceutical carrier.

Said upper gastro-intestinal disorders especially are those due to hyperacidity or to adverse effects of drugs and include esophagitis, gastritis and gastroduodenitis. Hyaluronic acid and chondroitin sulfate of the present formulation are preferably used as alkaline salt thereof such as sodium or potassium with a preference for sodium.

The method is carried out by orally administering to said human being from 80 mg to 200 mg of hyaluronic acid and from 150 mg to 500 mg of chondroitin sulfate once to four times/day in said pharmaceutical composition.

For the intended use, the association of chondroitin sulfate and hyaluronic acid is mixed with pharmaceutical carriers commonly used for the preparation of compositions for oral administration.

Thus, it is another object of the present invention to provide a glycosaminoglycan oral composition comprising (a) hyaluronic acid; and (b) chondroitin sulfate;

in admixture with a pharmaceutical carrier.

Said oral compositions comprising hyaluronic acid or a pharmaceutically acceptable salt thereof and chondroitin sulfate or a pharmaceutically acceptable salt thereof are practically protein-free. The hyaluronic acid component (a) usually has an average molecular weight of not less than $10^5$ Da. The chondroitin sulfate active ingredient (b) has an average molecular weight of from 5,000 to 50,000, advantageously from 10,000 to 50,000, preferably from 12,000 to 30,000.

The compositions of the invention are in appropriate oral unit forms such as tablets, powders or granulates in sachets, or suitably measured oral solutions or suspensions. Said unit forms contain from 80 mg to 200 mg of hyaluronic acid and from 150 mg to 500 mg of chondroitin sulfate.

Thus, according to an embodiment, the invention provides a glycosaminoglycan oral composition comprising (a) from 80 mg to 200 mg of hyaluronic acid or a pharmaceutically acceptable salt thereof having an average molecular weight of not less than $10^5$ Da; and (b) from 150 mg to 500 mg of chondroitin sulfate or a pharmaceutically acceptable salt thereof having an average molecular weight of from 5,000 to 50,000 Da;

in admixture with a pharmaceutical carrier.

Carriers for tablets include for example starches, cellulose and derivatives thereof; lubricants such as talc, stearic acid or magnesium stearate; diluents such as talc, powdered cellulose, lactose, polyethylenglycol, starches such as maize or corn starch, mannitol, sorbitol; disaggregating agents such as microcrystalline cellulose or crospovidone; ligands such as methylcellulose, sodium carboxymethylcellulose; sweeteners, such as saccharose, dextrose, mannitol, saccharin; or flavoring agents such as natural or synthetic oils.

Carriers for orally disintegrable (by mastication) tablets include for example lubricants, aggregating, sweetening, flavoring, bioadhesive or disaggregating agents. Carriers for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally chewable tablets and the liquid suspensions or solutions may be natural, optional reduced sugars such as sucrose, dextrose, xylitol, mannitol or sorbitol, or synthetic product such as sodium saccharine or aspartame. The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

According to a preferred embodiment, the compositions of the present invention are formulated in oral, preferably liquid, formulation wherein the active ingredients are mixed with a bioadhesive agent which is capable to adhere to the esophagus wall together with the chondroitinsulfate/ialuronic acid association active ingredient, thus protecting or healing the possibly damaged epithelium.

The composition thus prepared has the advantage to have a relatively low viscosity, i.e. from 30 to 100 mPa.

Bioadhesive molecules are substances very well known for their capacity to make active principles to adhere to the sites of action for local drug administration or to coat certain parts of the body.

When these bioadhesive molecules are administered to the upper part of the gastrointestinal tract, it is very easy that they are washed off from the site of activity by mucus and saliva, sometimes together with the active principle, especially if they contain it for the use in particular sites. This washing off is due to the low strength of the binding of bioadhesive molecules to the tissue surfaces.

In the case of a solution, this composition shall have also a viscosity useful for the administration of the active principle using a simple or monodose container in a reproducible form immediately ready for the consumers.

Thus, according to this preferred embodiment the present invention provides a glycosamonoglycan liquid oral composition comprising (a) hyaluronic acid at a concentration of from 0.75 to 1.5% by weight;

(b) chondroitin sulfate at a concentration of from 1.5 to 4% by weight; and (c) at least one bioadhesive polymer at a total concentration of from 3 to 6% by weight in water.

Since hyaluronic acid and chondroitin sulfate are by themselves polymers with high viscosity properties and bioadhesive activity, it is suitable to use polymers fully compatible with these active principles.

Said compatible bioadhesive polymers are advantageously selected from the group consisting of poloxamers such as. copolymers of ethylene oxide and propylene, in particular the products known under the trade name Lutrol®, polymers of vinylpyrrolidone, such as Polyvinylpyrrolidone Kw 24-32, corresponding to a molecular weight of 40,000, and cellulose derivatives such as hydroxypropyl cellulose.

Preferably, said hydrosoluble viscosity agents having high bioadhesive properties, such as poloxamer (Lutrol), polyvinylpyrrolidone or hydroxypropylcellulose, are mixed with hyaluronic acid having a molecular weight between 100 and 3,000 Kdalton and a chondroitin sulfate with a molecular weight between 5 and 40 Kdalton to obtain a clear solution with a viscosity between 30 and 100 mPa. Said solution can be easily used as a liquid pharmaceutical form having a very good activity in protecting the esophageal epithelium, thus preventing esophagitis due either to adverse effect of drugs such as, for example, oral biphosphonates or to gastric reflux, and to treat esophagites.

Beside the main components (a)-(c), the preferred compositions of the present invention may contain preservative agents to improve the stability of the composition as well as, sweetening, flavoring and, optionally, dying agents to improve and optimize the organoleptic characteristics of the liquid oral preparation.

Preservatives, such as sodium benzoate, sorbic acid and its salts, in particular potassium sorbate, EDTA or salts thereof, may be present at a concentration of from 0.01 to 0.4% by weight.

The sweetening agents may be natural, optional reduced sugar such as sucrose, dextrose, xylitol, mannitol or sorbitol, or synthetic product such as sodium saccharine or aspartame. Synthetic sweeteners may be present in a percentage of from 0.1 to 5% while the natural, optional reduced sugar may be present at a percentage of from 10% to 20%, preferably of from 15% to 20%.

The flavoring agents will be chosen by the expert in the field in relation to the organoleptic properties of the composition. The flavoring agents may be selected from the group consisting of pharmaceutically or nutritionally acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon, and grapes may be advantageously used. Preferred flavoring agents are those giving mint or fruit, such as grape, cherry or citrus, in particular orange and lemon, flavors or mixtures thereof. Flavoring agents, usually supported on a solid matrix, are generally present at a concentration of from 0.5 to 1.5%.

Dyes may be usually present at a concentration of 0.01-0.02%.

The pH of the liquid composition is from 4 to 6, preferably of from 4.8 to 5.2.

The viscosity of the solution is preferably from 40 to 70 mPa.

Advantageously, the preferred glycosaminoglycan oral liquid compositions of the present invention are aqueous solutions preferably in dosage unit form each one containing:

(a) hyaluronic acid in an amount of from 80 to 200 mg;

(b) chondroitin sulfate in an amount of from 150 to 500 mg; and (c) at least one bioadhesive polymer in a total amount of from 300 to 750 mg, said dosage unit being formed by an amount of water of from 10 to 13 g.

Generally, said dosage unit form may also comprise, beside the components (a)-(c), preservative, sweetening, flavoring—and optionally, dying agents in the above mentioned percentage. In particular, said preservatives are in a total amount corresponding to a concentration of from 0.01 to 0.4% by weight of the solution, said sweetening agents are in a total amount corresponding to a concentration of from 10 to 20% by weight of the solution when they are optionally reduced sugars and from 0.1 to 5% when they are synthetic sweeteners; said flavoring agents are in a total amount corresponding to a concentration of from 0.5 to 1.5% by weight of the solution and said optional dying agents are in a total amount corresponding to a concentration of from 0.01 to 0.02% by weight of the solution. The preferred pH of the solution is 4.8-5.2.

In particularly preferred oral liquid compositions, said hyaluronic acid has an average molecular weight of from $10^5$ to $10^6$ Da, said chondroitin sulfate has an average molecular weight of from 10,000 to 50,000 Da and the pH of the solution is from 4.8 to 5.2.

The dosage units can be welded sachets, glass or plastic little bottles or any other container offered by the current technology, included multidose containers.

The preferred oral liquid compositions of the present invention can be prepared by the known pharmaceutical technology methods.

In said oral liquid compositions compositions of the present invention, both hyaluronic acid and chondroitin sulfate are present as alkaline salt thereof, such as sodium or potassium, with a preference for sodium.

According to a further aspect, the invention provides a method for the preparation of a liquid oral composition, characterized by the fact that (A) hyaluronic acid, chondroitin sulfate and xylitol are dissolved in water by heating to 60° C. under vigorous stirring to obtain a clear solution, if necessary vacuum is applied till a maximum of 0.7 bar. The solution is maintained under moderate stirring for 30 minutes. To the solution previously obtained the bioadhesive polymer or the mixture of bioadhesive polymers are added maintaining a moderate stirring under vacuum till a maximum of 0.7 bar for 15 minutes. The stirring is maintained for further 30 minutes. The temperature is then decreased to 25° C.;

(B) the preservatives, the sweeteners, the dyes and the flavoring agents are dissolved in water under stirring at room temperature till complete solubilization;

(C) to the solution obtained in step (A) the solution obtained in step (B) is added maintaining under moderate stirring at 25° C. for 15 minutes. The pH is measured and 4M hydrochloric acid is added to reach a pH in a range between 4.8 and 5.2.

The preferred glycosaminoglycan liquid oral compositions according to the present invention are useful for the easy administration of combinations of hyaluronic acid and chondroitin sulfate also at high dosages in liquid form having the suitable bioadhesive properties. In particular, they are composition for the treatment of the upper gastrointestinal tract endothelial pathologies and, more specifically, for the prevention of esophagitis in case of esophageal reflux or for the treatment of diagnosed gastritis and esophagitis.

The efficacy of this preferred glycosaminoglycan liquid oral composition has been clinically evidenced in patients with esophagitis and gastritis symptoms. The study was a double blind drug versus placebo trial. After esophagogastroscopy and urea breath test, the patients were submitted to administration of the composition of the invention (Example 1). The results, based on symptoms analysis, showed statistically significance effectiveness of the composition against placebo. Also the pre-post treatment endoscopic investigations showed improvement of inflammation and healing of the mucosa in oesophageal or gastroduodenal pathology.

The following examples illustrate the invention. In said Examples, a purified, extractive sodium hyaluronate having an average molecular weight of about $10^6$ Da. and a purified, extractive sodium chondroitin sulfate having an average molecular weight of about 30,000 Da were used.

Example 1

(A) In a blender with sleeve and a blade stirrer, 120 g of sodium hyaluronate, 300 g of sodium chondroitin sulfate, 2,160 g of xylitol and 6.5 kg of deionized water are added. The temperature is maintained at 60° C. and vigorously stirred till complete dissolution. Then 240 g of Lutrol F127 and 240 g of Polyvinylpirrolidone KW 24-32 are added maintaining the stirring and the vacuum for 15 minutes till a clear solution is obtained. The stirring is maintained for further 30 minutes, then the temperature is lowered to 25° C.

(B) In a blender with magnetic stirring 9 g of sodium benzoate in powder, 18 g of potassium sorbate in powder, 24 g of flavoring agent, 18 g of dying agent and 1.5 g of deionized water are added. A moderate stirring is maintained till a clear solution is obtained.

(C) In the blender containing the solution obtained in step (A) the solution obtained in step (B) is added, maintaining the moderate stirring and the temperature at 25° C. for 15 minutes. The pH of the solution is 6.8, then the pH is lowered to less than 5.2 with 4M hydrochloric acid.

12 kg of a solution to be introduced into 1,000 dosage units are obtained with the following composition:

| | |
|---|---|
| Sodium hyaluronate | 120.0 mg |
| Sodium chondroitin sulfate | 300.0 mg |
| Lutrol F127 | 240.0 mg |
| Polyvinylpyrrolidone Kw 24-32 | 240.0 mg |
| Xylitol C | 2,160.0 mg |
| Sodium benzoate | 8.0 mg |
| Potassium sorbate | 24.0 mg |
| Flavoring agent | 24.0 mg |
| Dying agent | 1.8 mg |
| Deionized water to | 12,000.0 mg |

pH = 5.04
viscosity = 41 mPa

Example 2

By operating as described in Example 1, adding in step (A) 300 g of hydroxypropylcellulose instead of Lutrol F127, about 12 kg of solution to be introduced into 1,000 dosage units with the following composition are obtained:

| | |
|---|---|
| Sodium hyaluronate | 120.0 mg |
| Sodium chondroitin sulfate | 300.0 mg |
| Hydroxypropylcellulose | 240.0 mg |
| Polyvinylpyrrolidone Kw 24-32 | 240.0 mg |
| Xylitol C | 2,160.0 mg |
| Sodium benzoate | 8.0 mg |
| Potassium sorbate | 24.0 mg |
| Flavoring agent | 24.0 mg |
| Dying agent | 1.8 mg |
| Deionized water to | 12,000.0 mg |

pH = 4.95
viscosity = 60 mPa

Example 3

By operating as described in Example 1, adding in step (A) 100 g of sodium hyaluronate, 400 g of sodium chondroitin sulfate and 400 g of Lutrol F127 without the addition of polyvinylpirrolidone, about 12 kg of solution to be introduced into 1,000 dosage units with the following composition are obtained:

| | |
|---|---|
| Sodium hyaluronate | 100.0 mg |
| Sodium chondroitin sulfate | 400.0 mg |
| Lutrol F127 | 400.0 mg |
| Xylitol C | 2,160.0 mg |
| Sodium benzoate | 8.0 mg |
| Potassium sorbate | 24.0 mg |
| Flavoring agent | 24.0 mg |

-continued

| | |
|---|---|
| Dying agent | 1.8 mg |
| Deionized water to | 12,000.0 mg |

pH = 4.8
viscosity = 52 mPa

Example 4

By operating as described in Example 2, adding in step (A) 150 g of sodium hyaluronate, 200 g of sodium chondroitin sulfate and 700 g of hydroxypropylcellulose with the addition of polyvinylpirrolidone in step (A), about 12 kg of solution to be introduced into 1,000 dosage units with the following composition are obtained:

| | |
|---|---|
| Sodium hyaluronate | 150.0 mg |
| Sodium chondroitin sulfate | 200.0 mg |
| Hydroxypropylcellulose | 700.0 mg |
| Xylitol C | 2,160.0 mg |
| Sodium benzoate | 8.0 mg |
| Potassium sorbate | 24.0 mg |
| Flavoring agent | 24.0 mg |
| Dying agent | 1.8 mg |
| Deionized water to | 12,000.0 mg |

pH = 4.8
viscosity = 52 mPa

Example 5

By operating as described in Example 1, adding 400 g of hydroxypropylcellulose without the addition of polyvinylpirrolidone in step (A), about 12 kg of solution to be introduced into 1,000 dosage units with the following composition are obtained:

| | |
|---|---|
| Sodium hyaluronate | 120.0 mg |
| Chondroitin sulfate | 300.0 mg |
| Lutrol F127 | 240.0 mg |
| Hydroxypropylcellulose | 400.0 mg |
| Xylitol C | 2,160.0 mg |
| Sodium benzoate | 8.0 mg |
| Potassium sorbate | 24.0 mg |
| Flavoring agent | 24.0 mg |
| Dying agent | 1.8 mg |
| Deionized water to | 12,000.0 mg |

pH = 5.1
viscosity = 65 mPa.

Example 6

In a pilot study involving 20 Helicobacter-free patients (10 females and 10 males), aged between 6 and 82 years, suffering from esophagitis and gastritis symptoms characterized by heartburn, epigastric pain, dyspepsia, meteorism and belching. Among these patients, eleven had long standing reflux disease inadequately treated with proton pump inhibitors and antacids. The patients, to whom any previous drug treatment had been withdrawn 5 days before the start up of the trial, were treated with the composition of Example 1. The composition was administered with the following schedule: one spoon, i.e. 15 ml of solution every 8 hours (far form the meals) and two spoons at the bed time along two weeks. The treatment was completely safe, no drop-out happened during the trial and the compliance of the product was very favorable. The effectiveness was very satisfactory, especially in kids with reflux and adults with biliary gastritis probably due to prompt neutralization of alkaline biliary fluid. As a result, 12 patients total symptoms remission, 7 patients had less than 60% symptoms reduction and one patient less than 30% symptoms reduction.

The invention claimed is:

1. A glycosaminoglycan oral composition in unit dosage form comprising (a) from 80 mg to 200 mg of hyaluronic acid or a pharmaceutically acceptable salt thereof having an average molecular weight of not less than $10^5$ Da; and (b) from 150 mg to 500 mg of chondroitin sulfate or a pharmaceutically acceptable salt thereof having an average molecular weight of from 5,000 to 50,000 Da;

in admixture with a pharmaceutical carrier, said composition being formulated in a formulation wherein active ingredients are mixed with a poloxamer as a bioadhesive agent which is capable to adhere to the esophagus wall together with said active ingredients.

2. The composition according to claim 1, having a viscosity of from 30 to 100 mPa.

3. The composition according to claim 1, having a pH of from 4 to 6.

4. The composition according to claim 1, wherein said hyaluronic acid has an average molecular weight of from $10^5$ to $10^6$ Da, said chondroitin sulfate has an average molecular weight of from 12,000 to 50,000 Da and pH is of from 4.8 to 5.2.

5. The composition according to claim 1, wherein both hyaluronic acid and chondroitin sulfate are purified products.

6. The composition according to claim 1, which is practically protein-free.

7. The composition according to claim 1, wherein both hyaluronic acid and chondroitin sulfate are in form of their sodium or potassium salts.

8. A method for treatment of esophagitis in human which comprises administering to said human a glycosaminoglycan oral composition comprising (a) from 80 mg to 200 mg of hyaluronic acid or a pharmaceutically acceptable salt thereof having an average molecular weight of not less than $10^5$ Da; and (b) from 150 mg to 500 mg of chondroitin sulfate or a pharmaceutically acceptable salt thereof having an average molecular weight of from 5,000 to 50,000 Da;

in admixture with a pharmaceutical carrier, said composition being formulated in a formulation wherein active ingredients are mixed with a poloxamer as a bioadhesive agent which is capable to adhere to the esophagus wall together with said active ingredients.

9. The method of claim 8, wherein both hyaluronic acid and condroitin sulfate are in form of their sodium or potassium salts.

10. The method of claim 8, wherein esophagitis is due to hyperacidity or to adverse effects of drugs.

11. The method of claim 8, wherein said oral composition is a liquid oral composition.

* * * * *